(12) United States Patent
Miller et al.

(10) Patent No.: US 8,389,744 B1
(45) Date of Patent: Mar. 5, 2013

(54) TTPO (5 6,7-TRITHIAPENTACENE-13-ONE) AND ITS DERIVATIVES: A NEW CLASS OF THERMALLY STABLE, PHOTOOXIDATIVELY RESISTANT ORGANIC SEMICONDUCTORS

(75) Inventors: Glen P. Miller, Lee, NH (US); Jeremy Kintigh, Dover, NH (US)

(73) Assignee: University of New Hampshire, Durham, NH (US)

( * ) Notice: Subject to any disclaimer, the term of this patent is extended or adjusted under 35 U.S.C. 154(b) by 0 days.

(21) Appl. No.: 13/270,712

(22) Filed: Oct. 11, 2011

(51) Int. Cl.
*C07D 341/00* (2006.01)
*H01L 35/24* (2006.01)

(52) U.S. Cl. ............... 549/31; 549/29; 549/30; 257/40; 257/48

(58) Field of Classification Search .............. 549/29, 549/31; 257/40, 48
See application file for complete search history.

(56) References Cited

U.S. PATENT DOCUMENTS

| | | | |
|---|---|---|---|
| 4,981,962 A | 1/1991 | Baumann et al. | |
| 5,347,144 A | 9/1994 | Garnier et al. | |
| 6,265,243 B1 | 7/2001 | Katz et al. | |
| 7,425,722 B2 * | 9/2008 | Ugawa et al. | 257/40 |
| 7,816,679 B2 * | 10/2010 | Ugawa et al. | 257/40 |
| 7,928,432 B2 * | 4/2011 | Nuckolls et al. | 257/40 |
| 8,232,550 B2 * | 7/2012 | Clough et al. | 257/40 |
| 2011/0130594 A1 | 6/2011 | Miller et al. | |

OTHER PUBLICATIONS

Zhang, et al., "Chalcogenoarene semiconductors: new ideas from old materials", Journal of Materials Chemistry, 2011, vol. 21, pp. 1329-1337.
Etienne, et al., Compt. Rend., 1954, pp. 64-66 (article in French with English abstract attached).
Koch, et al., "Molecular orientation dependent energy levels at interfaces with pentacene and pentacenequinone", Organic Electronics, vol. 7, Aug. 22, 2006, pp. 537-545.
Benor, et al., "Electrical stability of pentacene thin film transistors", Organic Electronics, vol. 8, Jun. 29, 2007, pp. 749-758.
Palayangoda, et al., "Synthesis of highly soluble and oxidatively stable tetraceno[2,3-b] thiophenes and pentacenes", Center for Photochemical Sciences, May 16, 2007, vol. 72, pp. 6584-6587.
Ono, et al., "Photooxidation and reproduction of pentacene derivatives substituted by aromatic groups", Tetrahedron, vol. 63, Jul. 13, 2007, pp. 9699-9704.
Tunnell, et al., "Printing-induced improvements of organic thin-film transistors", Organic Electronics, vol. 9, Feb. 29, 2008, pp. 507-514.
Daniel, et al., "The road towards large-area electronics without vacuum tools", ECS Transactions, vol. 3, No. 8, 2006, pp. 229-236.
Rogers, et al., "Paper-like electronic displays: large-area rubber-stamped plastic sheets of electronics and microencapsulated electrophoretic inks", Bell Laboratories, Lucent Technologies, Apr. 24, 2001, vol. 98, No. 9, pp. 4835-4840.
Shelton, "New Photovoltaic Acceptors: Synthesis and Characterization of Functionalized C-Fused Anthradithiophene Quinones", University of Kentucky Master's Theses, Paper 92, 2011, pp. 1-62.

* cited by examiner

*Primary Examiner* — Golam M M Shameem
(74) *Attorney, Agent, or Firm* — Pierce Atwood LLP; Kevin M. Farrell; David J. Wilson (57) ABSTRACT

The present invention is directed towards a new class of semi-conducting acene derivatives. These compounds are soluble species and they all possess superior thermal stability and photooxidative resistance as compared to their counterparts that lack the substitution patterns disclosed herein.

4 Claims, 4 Drawing Sheets

TTPO (5 6,7-TRITHIAPENTACENE-13-ONE) AND ITS DERIVATIVES: A NEW CLASS OF THERMALLY STABLE, PHOTOOXIDATIVELY RESISTANT ORGANIC SEMICONDUCTORS

The authors acknowledge the National Science Foundation (Nanoscale Science & Engineering Center for High-rate Nanomanufacturing, NSF-0425826) for financial support of this work. The Federal Government has a nonexclusive, non-transferable, irrevocable license in this invention on behalf of the United States. [37 CFR 401.14(b)].

BACKGROUND OF INVENTION

Traditionally, inorganic materials have dominated the electronic device industry. For example, silicon arsenide and gallium arsenide have been used as semiconductor materials, silicon dioxide has been used as an insulator material, and metals such as aluminum and copper have been used as electrode materials. In recent years, however, there has been an increasing research effort aimed at using organic materials rather than the traditional inorganic materials in electronic devices. Among other benefits, the use of organic materials may enable lower cost manufacturing of electronic devices, may enable large area applications, and may enable the use of flexible circuit supports for display backplane and integrated circuits.

Thin-film organic electronics promise lightweight, flexible, inexpensive devices produced using high rate, low cost, solution based methods like spin coating or reel-to-reel processing with compliant substrates (Rogers, J. A., et al., Proc. Nat. Acad. Sci., 2001, 98:4835-4840; Daniel, J. H., et al., ECS Tranactions, 2006, 3:229-236). In a low cost manufacturing environment, process steps like thermal annealing of thin-films to improve charge carrier mobilities (Tunnell, A. J., et al., Org. Electron, 2008, 9:507-514) should occur in air. Thus, it is important that the chosen organic semiconductor possesses both excellent photooxidative resistance and thermal stability.

A variety of organic semiconductor materials have been considered, the most common being fused aromatic ring compounds as exemplified by small molecules such as pentacene-containing compounds, tetracene-containing compounds, anthracene-containing compounds, bis(acenyl)acetylene compounds, and acene-thiophene compounds. Several polymeric materials have also been considered such as regioregular polythiophenes, which are exemplified by poly(3-alkylthiophene), and polymers having fused thiophene units or bis-thiophene units.

Due to the high charge carrier mobilities associated with its thin films, pentacene is one of the most widely utilized organic semiconductor compounds. However, its application in thin-film electronic devices is hindered by its lack of thermal stability, its poor solubility and its propensity to photo-oxidize (Ono, K., et al., Tetrahedron, 2007, 61:9699-9704; Palayangoda, S. S., et al., J. Org. Chem., 2007, 72:6584-6587; Etienne, A. and C. Beauvios, Compt. Rend., 1954, 239:64-66; Benor, A., et al., Org. Electron, 2007, 8:749-758; Koch, N., et al., Org. Electron, 2006, 7:537-545). Pentacene oxidation leads to diminished electronic device performance. Pentacene-6,13-dione forms upon photo-oxidation and has been implicated as a deep charge carrier trap that reduces charge carrier mobility (Koch, N., et al., Org. Electron, 2006, 7:537-545). Other organic semiconductors like polythiophene also suffer from a lack of stability. As a result, thin film organic electronic devices like organic photovoltaics (OPVs) have limited lifetimes, generally no longer than a few years. Moreover, organic semiconductors are generally excluded from high temperature applications like, for example, high temperature sensors and controllers.

Therefore, what is needed in the art is a soluble pentacene derivative that can be cast into a thin-film organic semiconductor material with greater thermal stability and greater photooxidative resistance than either pentacene or any of its presently known derivative compounds.

SUMMARY OF INVENTION

The present invention relates to novel and non-obvious organic semiconductor compounds (compositions) as well as the organic semiconductor thin films prepared from them and uses thereof. Presented herein, are embodiments of the present invention including novel and non-obvious pentacene-derived compounds that show surprising and exceptional thermal stability and photo-oxidative resistance together with thin-film field effect mobilities. Also provided are exemplary uses and devices incorporating the organic semi-conductor materials of the present invention.

Figure 1:
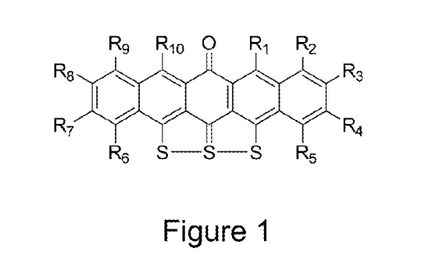
FIG. 1 shows a schematic representation of the generic compounds of the present invention.

The present invention relates to a new class of semi-conducting acene derivatives (organic semiconductor material) with the general structures shown in FIG. 1. These compounds are soluble species and they possess superior thermal stability and photooxidative resistance as compared to their counterparts that lack the substitution patterns shown.

In the present invention, we have discovered the molecular composition and structure of TTPO, 5,6,7-trithiapentacene-13-one, $C_{22}H_{10}S_3O$. We have also discovered that TTPO behaves as an organic semiconductor with several exceptional properties: (i) thermal stability up to and including 450° C.; (ii) a propensity to crystallize in a head-to-tail π-π stacking configuration that is ideal for electron and hole conduction through thin films (i.e., charge carrier mobility); (iii) solubility in organic solvents; (iv) ease of preparation; (v) a synthetic procedure amenable to scale-up; (vi) variable temperature transistor behavior with increasing charge carrier mobilities at increasing temperatures, suitable for high temperature electronic applications; (vii) amenable to thermal evaporation techniques for the fabrication of high quality thin films.

With regards to the structures (FIG. 1), $R_1$ through $R_{10}$ represent any functional group, organic or otherwise. This would include, without limitation, hydrogen, alkyl moieties (e.g., methyl, ethyl, propyl, isopropyl, n-butyl-, isobutyl, sec-butyl, t-butyl, etc.), aryl moieties (e.g., phenyl and substituted phenyl groups including but not limited to o-dialkylphenyl), heteroaryl (e.g., thiophene and substituted thiophenes), carbonyl moieties, alkene moieties, alkyne moieties, diene moieties, the nitrile moiety, the trifluoromethyl moiety, halogen (e.g., F, Cl, Br, I) moieties, alkylthio (e.g., simple alkylthio groups including but limited to decylthio as well as complex alkylthio groups including but limited to phenethylthio), arylthio, alkynyl (e.g., simple alkynyl $[C_2H]$ and substituted alkynyl including but not limited to phenylethynyl and trialkylsilylethynyl).

The intermolecular interactions known as π-π-stacking interactions are desirable in organic semiconductor thin film materials of the present invention. Thus, the thin film materials of the present invention should have a π-π-stacking structure although the present application is not limited thereto. It is known that crystalline thin-films of pentacene (i.e., without trithia and ketone functional groups) possess a herringbone structure. As compared with this herringbone structure, a π-π-stacking structure in which aromatic rings on adjacent molecules are stacked above and below each other in a parallel fashion [see crystal structure in FIGS. 3 and 4 in which adjacent molecular planes are stacked with respect to each other (adjacent molecular planes have parallel overlapping portions)] can realize greater π-π overlap throughout the thin-film leading to desirable electronic characteristics including charge carrier mobilities.

DETAILED DESCRIPTION OF INVENTION

Prior Art

Acene quinones like naphthalene-1,4-dione (I), anthracene-9,10-dione (II), tetracene-5,12-dione (III) and pentacene-6,13-dione (IV) are all well known compounds with relatively large HOMO-LUMO gaps that make them unsatisfactory for organic semiconductor applications.

I

II

III

IV

Exocyclic heteroacenes bearing either sulfur (S), selenium (Se) or tellurium (Te) atoms are well known species and have been extensively described. Recently, for example, Lei Zhang and co-workers summarized the entire set of known exocyclic heteroacenes (see: *Materials Chemistry*, 2011, volume 21, pages 1329-1337 and references therein). The known set of exocyclic heteroacenes includes compounds V-X, all of which have either two or three linearly fused benzene rings (that is, naphtahelene based or anthracene based exocyclic heteroacenes) and relatively large HOMO-LUMO gaps that are not well suited for organic semiconductor applications. Compounds like VI, VIII and X require a synthesis that utilizes toxic selenium or tellurium.

V

VI

VII

VIII

IX

X

The known set of exocyclic heteroacenes also includes compounds XI-XVII as summarized by Lei Zhang and co-workers (*Materials Chemistry*, 2011, volume 21, pages 1329-1337). All of these compounds suffer from poor solubility and they are produced using undesirable synthetic processes. For example, hexathianthracene (XI), dithiatetracene (XII), tetrathiatetracene (XIII), and hexathiapentacene (XVII) are ordinarily synthesized by reacting a suitable precursor with an excess of sulfur powder in hot solvent. This process leads to considerable quantities of undesirable, insoluble by-products such as polysulfides and mixtures of di- and tetra-substituted products. Compounds XIV, XV and XVI require a synthesis that utilizes toxic selenium and tellurium.

XI

XII

XIII

XIV

XV

XVI

XVII

None of the known compounds I-XVII or other known structures contain a combination of ketone and trithia substituents on a pentacene framework as in the compounds of the present invention. None of the known compounds I-XVII or other known structures are prepared using the readily available 6,13-dihydro-6,13-dihydroxypentacene precursor as in the synthesis process described in the present invention. None of the known compounds I-XVII or other known structures possess the same combination of solubility, thermal stability, and photoxidative stability as the compounds of the present invention.

Compounds of the Present Invention

The compounds of the present invention relate to novel and non-obvious acene derivatives. Acenes or large acenes or oligoacenes or polyacenes are a class of organic compounds and polycyclic aromatic hydrocarbons made up of linearly fused benzene rings. Pentacene contains five linearly fused benzene rings. Although the structure of pentacene resembles that of other aromatic compounds like anthracene, its aromatic properties are poorly defined by those of skill in the art and; as such, pentacene and its derivatives are the subject of much research.

The compounds of the present invention are acene derivatives bearing functional groups. FIG. 1 shows a schematic of the generic compounds of the present invention where $R_1$ through $R_{10}$ represent any group chosen from the following list: hydrogen, alkyl (e.g., methyl, ethyl, propyl, isopropyl, n-butyl-, isobutyl, sec-butyl, t-butyl, etc.), aryl (e.g., phenyl and substituted phenyl groups including but not limited to o-dialkylphenyl), heteroaryl (e.g., thiophene and substituted thiophenes), nitrile, carbonyl, trifluoromethyl, halogen (e.g., F, Cl, Br, I), alkylthio (e.g., simple alkylthio groups including but limited to decylthio as well as complex alkylthio groups including but limited to phenethylthio), arylthio, alkynyl (e.g., simple alkynyl [$C_2H$] and substituted alkynyl including but not limited to phenylethynyl and trialkylsilylethynyl).

TTPO and its Derivatives.

We also contemplate larger acene derivatives based on this basic structure with some combination of trithia and ketone functional groups. For example, hexacene, heptacene, octacene and nonacene systems with 1-3 sets of trithia and ketone functional groups are contemplated herein.

Figure 5:
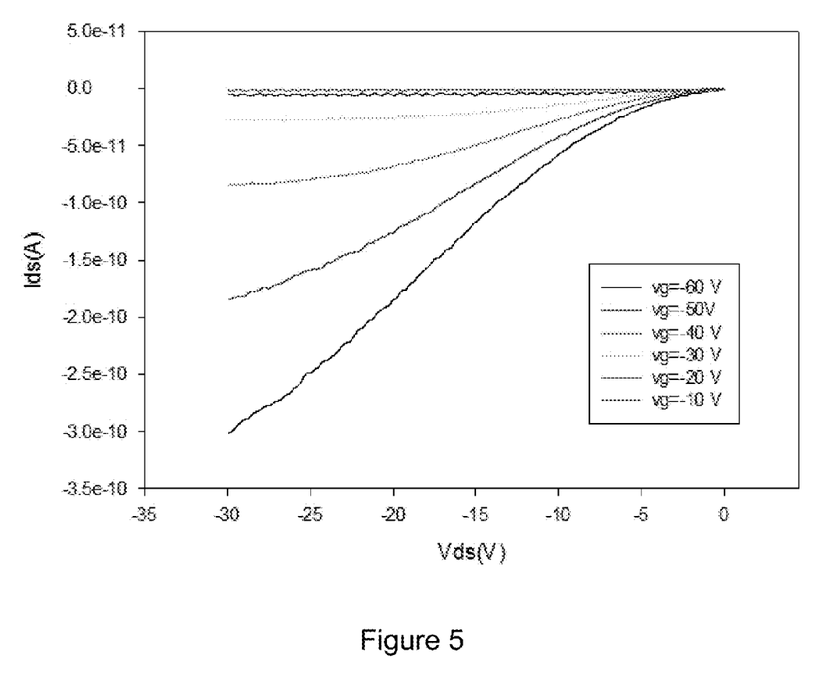
FIG. 5 shows TTPO's (5,6,7-trithiapentacene-13-one, $C_{22}H_{10}S_3O$) organic thin-film transistor behavior at 125° C. Drain current versus drain-source voltage are shown for several gate voltages. This device has a field-effect hole mobility of $1.27 \times 10^{-6}$ cm$^2$ V$^{-1}$ s$^{-1}$ at 75° C. and $8.05 \times 10^{-6}$ cm$^2$ V$^{-1}$ s$^{-1}$ at 100° C.

FET Studies of Thin-Films. In addition to possessing superior thermal stabilities and photo-oxidative resistances, TTPO and its derivatives are soluble in a variety of organic solvents and therefore represent excellent candidates for organic thin-film electronic devices prepared using low cost, roll-to-roll manufacturing techniques. Because of its superior thermal stability, organic thin-film electronic devices of TTPO and its derivatives may also be prepared using techniques like thermal evaporation. An organic thin-film transistor (OTFT) prepared from TTPO showed a field effect mobility of $1.27 \times 10^{-6}$ cm$^2$ V$^{-1}$ s$^{-1}$ at 75° C. and $8.05 \times 10^{-6}$ cm$^2$ V$^{-1}$ s$^{-1}$ at 100° C. (see FIG. 5 for drain-source current versus drain-source voltage behavior as a function of gate voltage). Given the enhanced thermal stability and photo-oxidative resistance of TTPO and its derivatives, these compounds represent a superior class for organic thin-film electronic devices including devices to be utilized at high temperatures like, for example, sensors and controls, transistors, organic photovoltaics and organic light emitting devices.

Uses of the Present Invention

The acene derivatives disclosed herein are useful as organic semiconductor materials in semiconductor devices. Although there are numerous types of semiconductor devices, common to all is the presence of one or more semiconductor materials. Semiconductor devices include, for example, rectifiers, transistors (of which there are many types including p-n-p, n-p-n and thin-film transistors), light emitting semiconductors devices (for example, organic light emitting diodes), photoconductors, current limiters, thermistors, p-n junctions, field-effect diodes, Scottky diodes and other devices known in the art. In each semiconductor device, the semiconductor material is combined with one or more conductors or insulators to form the device. Semiconductor devices can be prepared or manufactured by known methods such as, for example, those described by Peter Van Zant in *Microchip Fabrication*, Fourth Edition, McGraw-Hill, New York (2000).

Electronic devices include components such as, e.g., transistors, arrays of transistors, diodes, capacitors, embedded capacitors and resistors that are used to form circuits. Electronic devices also include, for example, arrays of circuits that perform an electronic function. Examples of these arrays or integrated circuits are amplifiers, receivers, transmitters and oscillators.

Applications of these devices and arrays include, for example, radio frequency identification devices (RFIDs), smart cards, lamps, displays and the like. The present invention is not limited by the type of the device.

A particularly useful type of transistor device, e.g., the thin-film transistor (TFT), generally includes a gate electrode, a gate dielectric on the gate electrode, a source electrode and a drain electrode adjacent to the gate dielectric, and a semiconductor layer adjacent to the gate dielectric and adjacent to the source and drain electrodes [see, for example, S. M. Sze, Physics of Semiconductor Devices, 2nd edition, John Wiley and Sons, page 492, New York (1981)]. These components can be assembled in a variety of configurations. More specifically, an organic thin-film transistor (OTFT) has an organic semiconductor layer.

Typically, a substrate supports the OTFT during manufacturing, testing, and/or use. Optionally, the substrate can provide an electrical function for the OTFT. Useful substrate materials include organic and inorganic materials. For example, the substrate can comprise inorganic glasses, ceramic foils, polymeric materials (for example, acrylics, epoxies, polyamides, polycarbonates, polyimides, polyketones, poly(oxy-1,4-phenyleneoxy-1,4-phenylenecarbonyl-1,4-phenylene) (sometimes referred to as poly(ether ether ketone) or PEEK), polynorbornenes, polyphenyleneoxides, poly(ethylene naphthalenedicarboxylate) (PEN), poly(ethylene terephthalate) (PET), poly(phenylene sulfide) (PPS), filled polymeric materials (for example, fiber-reinforced plastics (FRP)), and coated or uncoated metallic foils.

The gate electrode can be any useful conductive material. For example, the gate electrode can comprise doped silicon, or a metal, such as aluminum, chromium, gold, silver, nickel, palladium, platinum, tantalum, and titanium. Conductive polymers also can be used, for example polyaniline or poly(3,4-ethylenedioxythiophene)/poly(styrene sulfonate) (PEDOT:PSS). In addition, alloys, combinations, and multilayers of these materials can be useful. In some OTFTs, the same material can provide the gate electrode function and also provide the support function of the substrate. For example, doped silicon can function as the gate electrode and support the OTFT.

The gate dielectric is generally provided on the gate electrode. This gate dielectric electrically insulates the gate electrode from the balance of the OTFT device. Useful materials for the gate dielectric can comprise, for example, an inorganic electrically insulating material or a polymeric dielectric layer.

Specific examples of materials useful for the gate dielectric include strontiates, tantalates, titanates, zirconates, aluminum oxides, silicon oxides, tantalum oxides, titanium oxides, silicon nitrides, barium titanate, barium strontium titanate, barium zirconate titanate, zinc selenide, and zinc sulfide. In addition, alloys, combinations, and multilayers of these materials can be used for the gate dielectric.

Alternatively, the gate dielectric may comprise an organic polymeric dielectric layer. A number of organic polymers have been considered as dielectric materials. These include polyimides, parylene C, crosslinked benzocyclobutene, and cyanoethylpullulan [see, for example, C. D. Sheraw et al., "Spin-on polymer gate dielectric for high performance organic thin film transistors", Materials Research Society Symposium Proceedings v 558, Materials Research Society, Warrendale, Pa., USA, pages 403-408 (2000); U.S. Pat. No. 6,265,243 (Katz); and U.S. Pat. No. 5,347,144 (Garnier)].

The source electrode and drain electrode are separated from the gate electrode by the gate dielectric, while the organic semiconductor layer can be over or under the source electrode and drain electrode. The source and drain electrodes can be any useful conductive material. Useful materials include most of those materials described above for the gate electrode, for example, aluminum, barium, calcium, chromium, gold, silver, nickel, palladium, platinum, titanium, polyaniline, PEDOT:PSS, other conducting polymers, alloys thereof, combinations thereof, and multilayers thereof. Some of these materials are appropriate for use with n-type semiconductor materials and others are appropriate for use with p-type semiconductor materials, as is known in the art.

The thin film electrodes (that is, the gate electrode, the source electrode, and the drain electrode) can be provided by any useful means such as physical vapor deposition (for example, thermal evaporation or sputtering) or ink jet printing. The patterning of these electrodes can be accomplished by known methods such as shadow masking, additive photolithography, subtractive photolithography, printing, microcontact printing, and pattern coating.

One particularly useful method of preparing thin film transistors or integrated circuits is by means of a flexible, repositionable polymeric aperture masks to create integrated circuits or integrated circuit elements. The techniques involve sequentially depositing material through a number of polymeric aperture masks formed with patterns that define layers, or portions of layers, of the circuit. In some embodiments, circuits can be created solely using aperture mask deposition techniques, without requiring any of the etching or photolithography steps typically used to form integrated circuit patterns. The techniques can be particularly useful in creating circuit elements for electronic displays such as liquid crystal displays and low-cost integrated circuits such as radio frequency identification (RFID) circuits. In addition, the techniques can be advantageous in the fabrication of integrated circuits incorporating organic semiconductors, which typically are not compatible with photolithography or other wet processes.

In various embodiments, different repositionable aperture masks such as flexible aperture masks, free-standing aperture masks and polymeric aperture masks formed with patterns may be used to define a layer or a portion of a layer of an integrated circuit. Repositionable polymeric aperture masks may have a thickness of from approximately 5 to 50 microns or from approximately 15 to 35 microns. The various deposition apertures in the aperture masks may have widths less than approximately 1000 microns, less than approximately 50 microns, less than approximately 20 microns, less than approximately 10 microns, or even less than approximately 5 microns. Apertures of these sizes are particularly useful in creating small circuit elements for integrated circuits. Moreover, one or more gaps between deposition apertures may be less than approximately 1000 microns, less than approximately 50 microns, less than approximately 20 microns or less than approximately 10 microns, which is also useful in creating small circuit elements. Also, aperture masks that include a pattern having a width greater than approximately 1 centimeter, 25 centimeters, 100 centimeters, or even 500 centimeters are also described. Patterns having these widths can be useful in creating various circuits over a larger surface area as described in greater detail below. In some embodiments, layer may be deposited on a substrate through repositionable polymeric aperture masks.

Various laser ablation techniques may be used to facilitate the creation of polymeric aperture masks having patterns of deposition apertures. In addition, stretching techniques and other techniques may be used to facilitate alignment of flexible polymeric aperture masks. Furthermore, methods of controlling sag in aperture masks may be used which can be particularly useful in using masks that include a pattern that extends over a large width.

The aperture masks can provide a number of advantages. For example, the aperture masks can facilitate the creation of relatively small circuit elements using deposition processes. The aperture masks can facilitate circuit elements having widths less than approximately 1000 microns, less than approximately 50 microns, less than approximately 20 microns, less than approximately 10 microns, or even less than approximately 5 microns. Also, the aperture masks can facilitate the creation of relatively large circuit patterns, in some cases having circuit elements of the relatively small widths mentioned above that cover large areas (such as 10 square centimeters, 50 square centimeters, 1 square meter, or even larger areas). In addition, the aperture masks can reduce costs associated with circuit fabrication, and in the case of organic semiconductors, can even improve device performance. Polymeric aperture masks can be created using a laser ablation process that may be faster and less expensive than other techniques. Also, inexpensive polymeric materials can allow the polymeric masks to be disposable, although reusable embodiments are also described.

In addition, polymeric material may be well suited to be impregnated with magnetic material. In that case, the magnetic material may be used to reduce sag in the mask as described below. Furthermore, polymeric material is often stretchable, which allows the mask to be stretched to either reduce sag or to align the mask.

The compounds of the invention can be used alone or in combination as the organic semiconductor layer of the OTFT (or other semiconductor device). The layer can be provided by any useful means, such as, for example, vapor deposition and printing techniques.

The compounds of the invention can be used in integrated circuits comprising a plurality of OTFTs, as well as in various electronic articles. Such articles include, for example, radio-frequency identification (RFID) tags, backplanes for flexible displays (for use in, for example, personal computers, cell phones, or handheld devices), smart cards, memory devices, and the like.

The invention now being described, it will be apparent to one of ordinary skill in the art that many changes and modifications can be made thereto without departing from the spirit or scope of the invention.

As defined herein and as understood by those of ordinary skill in the art the art, HOMO and LUMO are acronyms for "Highest Occupied Molecular Orbital" and "Lowest Unoccupied Molecular Orbital," respectively. The difference of the energies of the HOMO and LUMO, termed the "HOMO-LUMO gap" for individual molecules and the "band gap" for collections of molecules in a thin-film can sometimes serve as a measure of the excitability of the molecule: the smaller the energy, the more easily it will be excited.

The HOMO level is to organic semiconductors and quantum dots what the valence band is to inorganic semiconductors. The same analogy exists between the LUMO level and the conduction band. The energy difference between the HOMO and LUMO level is approximately equal to the band gap energy.

When the molecule forms a dimer or an aggregate, the proximity of the orbitals of the different molecules induce a splitting of the HOMO and LUMO energy levels. This splitting produces vibrational sublevels which each have their own energy, slightly different from one another. There are as many vibrational sublevels as there are molecules that interact together. When there are enough molecules influencing each other (e.g., in an aggregate), there are so many sublevels that we no longer perceive their discrete nature: they form a continuum. We no longer consider energy levels, but energy bands. We no longer refer to the gap between filled and unfilled orbitals as the "HOMO-LUMO gap" but rather the "band gap".

EXEMPLIFICATION

General Remarks 1,4-benzquinone, sodium iodide, sodium borohydride and elemental sulfur were purchased from Aldrich (St. Louis,

Mo.). α,α,α',α'-tetrabromo-o-xylene and 1,2,4-trichlorobenzene were purchased from TCI America (Portland, Oreg.). All purchased reactants and reagents were used without further purification. All reactions, unless otherwise noted, were carried out under the protection of $N_2$. All reaction containers were flame dried under vacuum before use. Solvents were purified by standard methods and dried if necessary. $^1$H NMR (500 MHz) spectra were recorded with a Varian AC 500 spectrometer. $^1$H and $^{13}$C NMR samples were internally referenced to TMS (0.00 ppm). Mass spectra were determined on LDI-TOF-MS (Shimadzu-Biotech, Columbia, Md.) mass spectrometer.

6,13-Pentacenequinone

To a clear solution of α,α,α',α'-tetrabromo-o-xylene (30.5 g, 0.073 mol) in DMF (100 mL) was added benzoquinone (3.125 g, 0.03 mol) and sodium iodide (27.25 g, 0.18 mol). The resulting brown suspension was heated and stirred at 120° C. overnight. After cooling to RT, the yellow solids were filtered via vacuum filtration. The yellow solids were washed with water, saturated sodium bisulfite solution and dried to yield the product (8.1 g, 91%). $^1$H NMR (500 MHz, CDCl$_3$): δ 8.96 (s, 4H), 8.14 (m, 4H), 7.72 (m, 4H). $^{13}$C NMR (125.68 MHz, CDCl$_3$): δ 183.2, 135.47, 130.80, 130.30, 129.98, 129.66. m/z: 308 [W].

6,13-Dihydro-6,13-dihydroxypentacene

To a suspension of 6,13-pentacenequinone (1.0 g, 3.24 mmol) in dry MeOH (40 mL) at 0° C. under an argon atmosphere was slowly added NaBH$_4$ (1.22 g, 32.46 mmol). The reaction mixture was stirred at 0° C. for 0.5 h and at RT for 1 h, and then quenched with H$_2$O at 0° C. The resulting mixture was filtered and washed with H$_2$O. The resulting solid was taken up in CHCl$_3$, then filtered and washed with CHCl$_3$, and dried in vacuo to give product as an off-white solid (0.92 g, 91%): mp 235° C. $^1$H NMR (500 MHz, DMSO-d$_6$): δ 8.12 (s, 4H), 7.95 (m, 4H), 7.48 (m, 4H), 6.63 (s, 2H), 5.81 (s, 2H). $^{13}$C NMR (125.68 MHz, DMSO-d$_6$): δ 138.19, 131.67, 127.47, 125.44, 120.91, 66.98. LDI-MS m/z: 312 [M$^+$], 296 [M$^+$-OH], 280 [M$^+$-2(OH)]. For the purpose of synthesizing TTPO, the 6,13-dihydro-6,13-dihydroxypentacene prepared in this step may consist of all cis diastereomer compound, all trans diastereomer compound, or any mixture of cis and trans diastereomers in any proportion. For this reason, it is not necessary to isolate either cis or trans diastereomer.

TTPO: 5,6,7-Trithiapentacene-13-one

Figure 2:
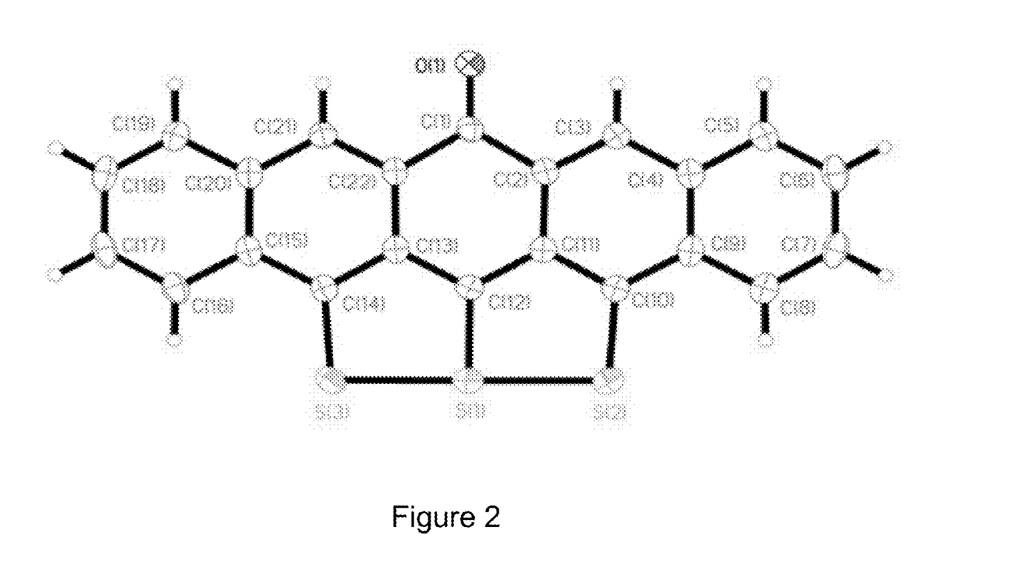
FIG. 2 shows the molecular structure of TTPO (5,6,7-trithiapentacene-13-one, $C_{22}H_{10}S_3O$) showing the crystallographic labeling scheme and displacement ellipsoids drawn at the 50% probability level. Hydrogen atoms are shown as spheres of arbitrary radii.
Figure 3:
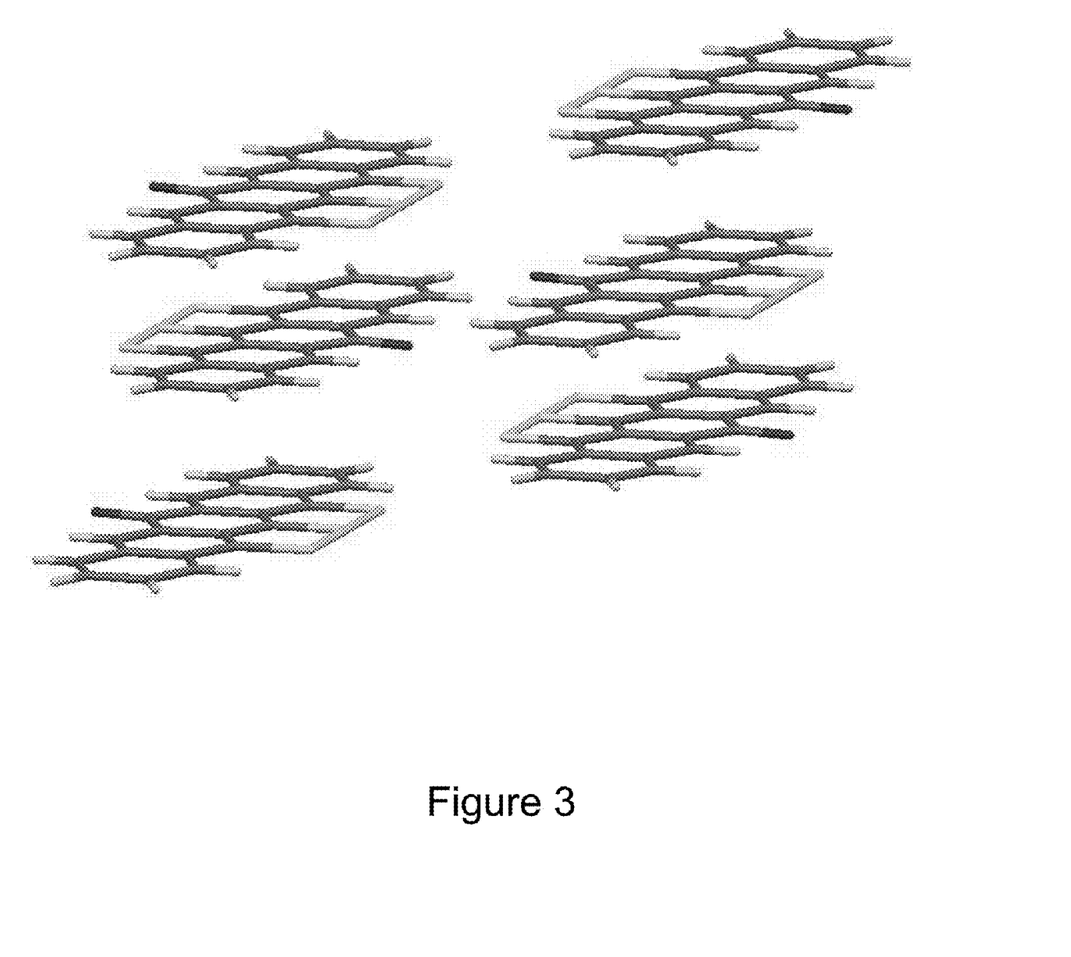
FIG. 3 shows the head-to-tail stacking in the crystal structure of TTPO (5,6,7-trithiapentacene-13-one, $C_{22}H_{10}S_3O$).
Figure 4:
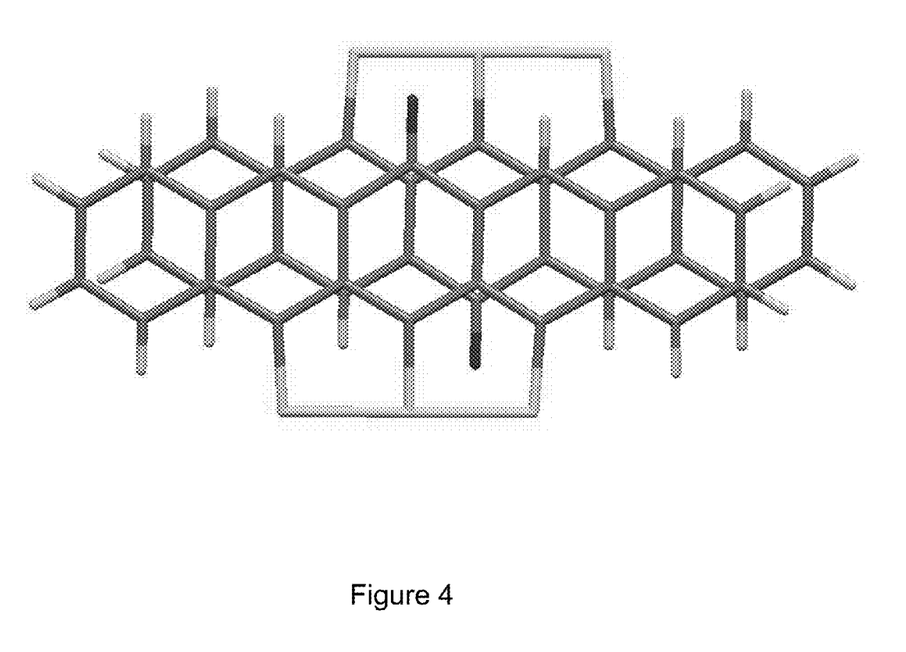
FIG. 4 shows two adjacent, π-π stacking molecules in the crystal structure of TTPO (5,6,7-trithiapentacene-13-one, $C_{22}H_{10}S_3O$) looking down the shortest intermolecular carbon-carbon contact.

Elemental sulfur (3.175 g, 99.1 mmol) was added to dry 1,2,4-trichlorobenzene (100 mL) and heated to 218° C. under an argon atmosphere until completely dissolved, followed by the addition of 6,13-dihydro-6,13-dihydroxypentacene (2.505 g, 8 mmol). The 6,13-dihydro-6,13-dihydroxypentacene may consist of all cis diastereomer compound, all trans diastereomer compound, or any mixture of cis and trans diastereomers in any proportion. The reaction mixture was stirred at 218° C. for 18 h and at then cooled to 25° C. The resulting mixture was filtered and washed with acetone then chloroform. The resulting solid was taken up in CHCl$_3$, then filtered and washed with CHCl$_3$ repeatedly until 6,13-pentacenequinone was no long detectable by NMR spectroscopy. The solid was dried in vacuo to give product as a purple solid with a metallic sheen (1.492 g, 48%): mp 388-392° C. $^1$H NMR (500 MHz, CDCl$_3$): δ 8.95 (s, 1H), 8.79-8.73 (m, 1H), 8.26-8.20 (m, 1H), 7.91-7.83 (m, 2H). LDI-MS m/z: 386 [W], 354 [M$^+$-S]. A crystal structure of TTPO has been determined (see FIGS. 2-4). FIG. 2 unequivocally demonstrates the chemical composition of TTPO by x-ray crystallography. FIGS. 3 and 4 illustrate the π-π stacking orientation of the TTPO molecules in the x-ray crystal structure.

What is claimed is:

1. A thermally stable and photooxidatively resistant acene organic semiconductor composition having the formula:

wherein $R_1$ through $R_{10}$ represent any group chosen from the following list: hydrogen, alkyl, aryl, heteroaryl, nitrile, carbonyl, trifluoromethyl, halogen, alkylthio, arylthio, simple alkynyl and substituted alkynyl.

2. The composition of claim 1, wherein said acene organic semiconductor composition is:

3. An electronic device comprising one or more of the acene organic semiconductor compositions of claim 1.

4. The electronic device of claim 3, wherein said acene organic semiconductor composition is:

* * * * *